US00PP30131P3

(12) United States Plant Patent
Schoone

(10) Patent No.: US PP30,131 P3
(45) Date of Patent: Jan. 22, 2019

(54) ***PHALAENOPSIS* ORCHID PLANT NAMED 'SWEET DAY'**

(50) Latin Name: *Phalaenopsis hybrida*
Varietal Denomination: Sweet Day

(71) Applicant: Floricultura, Heemskerk (NL)

(72) Inventor: René Schoone, Assendelft (NL)

(73) Assignee: FLORICULTURA, Heemskerk (NL)

( * ) Notice: Subject to any disclaimer, the term of this patent is extended or adjusted under 35 U.S.C. 154(b) by 0 days.

(21) Appl. No.: 15/731,128

(22) Filed: Apr. 25, 2017

(65) Prior Publication Data

US 2017/0311516 P1 Oct. 26, 2017

Related U.S. Application Data

(60) Provisional application No. 62/327,702, filed on Apr. 26, 2016.

(30) Foreign Application Priority Data

Apr. 29, 2016 (NL) ..... PBR OPS1325

(51) Int. Cl.
*A01H 5/02* (2018.01)

(52) U.S. Cl.
USPC ..... Plt./311
CPC ..... *A01H 5/02* (2013.01)

(58) Field of Classification Search
USPC ..... Plt./311
CPC ... A01H 5/02; A01H 5/08; A01H 5/00; A01H 6/62
See application file for complete search history.

(56) References Cited

PUBLICATIONS

Floricultura *Phalaenopsis* Lark Song 2018, retrieved on Apr. 12, 2018, retrieved from the Internet at https://www.floricultura.com/product/?cat=floriclone-phalaenopsis&prod=9765, one page. (Year: 2018).*

Tsai et al. Biogeography of the *Phalaenopsis amabilis* species complex inferred from nuclear and plastid DNAs (2015) BMC Plant Biology 15:202, 16 pp. (Year: 2015).*

* cited by examiner

*Primary Examiner* — June Hwu
(74) *Attorney, Agent, or Firm* — Foley & Lardner LLP; Sunit Talapatra

(57) ABSTRACT

A new and distinct *Phalaenopsis* plant named 'Sweet Day' particularly characterized by flowers which are light purple with some white; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Sweet Day'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Sweet Day'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Sweet Day' is a product of a controlled breeding program conducted by the inventor, René Schoone, in Strengweg, Heemskerk, The Netherlands.

The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Sweet Day' originated from a cross made by the inventor in 2003 in Strengweg, Heemskerk, The Netherlands. The female or seed parent is the *Phalaenopsis* cultivar designated 'Sogo Davis', unpatented.

The male or pollen parent is the *Phalaenopsis* cultivar designated *Phalaenopsis amabilis*, unpatented. The new *Phalaenopsis* 'Sweet Day' was discovered and selected by the inventor as a single flowering plant within the progeny of the stated cross in a controlled environment in 2011 in Strengweg, Heemskerk, The Netherlands.

Asexual reproduction of the new *Phalaenopsis* cultivar by tissue culture (mericloning) was first performed in November, 2011 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Sweet Day', which in combination distinguish this *Phalaenopsis* as a new and distinct cultivar:

1. flowers which are light purple with some white;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Sweet Day', the flowers of the female parent 'Sogo Davis' are purple/violet with a red lip and the flowers of the male parent *Phalaenopsis amabilis* are white, whereas the flowers of 'Sweet Day' are purple with some white.

Presently, the commercial cultivar to which 'Sweet Day' can be meaningfully compared is 'Lark Song'. The flower of 'Lark Song' are larger than the flower of 'Sweet Day'. Also the plant of 'Lark Song' is larger than the plant of 'Sweet Day'. The flower of 'Lark Song' has more overall purple coloration on the petals and less red/purple coloration on the midlobe.

BRIEF DESCRIPTION OF THE PHOTOGRAPHS

The accompanying photographs illustrate the overall appearance of the new *Phalaenopsis* 'Sweet Day' showing the colors as true as is reasonably possible with colored reproductions of this type. Colors in the photographs may differ slightly from the color values cited in the detailed botanical description, which accurately describe the color of 'Sweet Day'.

DETAILED BOTANICAL DESCRIPTION

Figure 1:
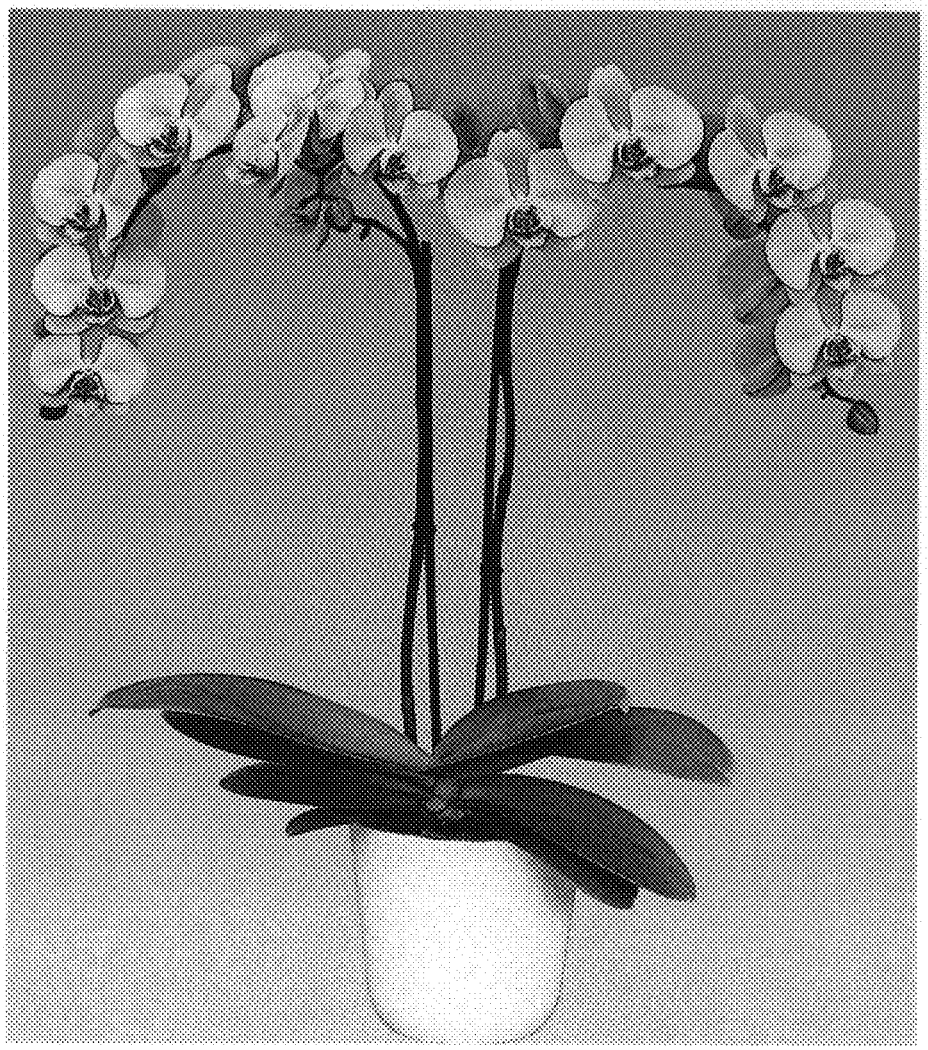
FIG. 1 shows a side view perspective of a typical flowering plant of 'Sweet Day' in a 12 cm pot, at 16 months of age.

The new *Phalaenopsis* cultivar 'Sweet Day' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Sweet Day' as grown in a greenhouse in Strengweg, Heemskerk, The Netherlands, under conditions which closely approximate those generally used in commercial practice. Initially, the ideal temperature to grow plants of 'Sweet Day' is 27° C. during the day and at night. Then, during the flowering phase of 'Sweet Day', the ideal growing temperature is 20-22° C. during the day and 18° C. at night. Light levels for growing 'Sweet Day' are a minimum of 5,000 lux and a maximum of 10,000 lux. A balanced fertilizer with level of 200 ppm N, 87 ppm P, 168 ppm K is applied. Duration of growth of 'Sweet Day' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Sweet Day' plants described is 12 months after potting.

Classification:

*Botanical.—Phalaenopsis hybrida.*

Parentage:

*Female or seed parent.—Phalaenopsis* cultivar designated 'Sogo Davis', unpatented.

*Male or pollen parent.—Phalaenopsis* cultivar designated *Phalaenopsis amabilis*, unpatented.

Propagation:

*Type.*—Tissue culture.

*Rooting habit and description.*—Fleshy; approximately 3 mm-7 mm wide and greyed/green in color (RHS 190A); freely branching. It takes 12 weeks for plants growing in tissue culture to initiate roots.

Plant:

*Size at maturity.*—Height (from bottom of pot to highest flower): about 60 cm. Spread: about 50 cm.

*Growth habit.*—Standard; green leaves (RHS N137A) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 racemes with flowers appear.

Foliage:

*Quantity per plant.*—About 6-8 leaves are produced before flowering.

*Arrangement and attachment.*—Alternate, clasping.

*Overall shape of leaf.*—Oval; the tip is blunt and asymmetric.

*Texture (upper & underside).*—Smooth and leathery.

*Pubescence.*—None.

*Mature leaf length.*—About 15 cm.

*Mature leaf width.*—About 7 cm.

*Mature leaf thickness.*—About 2 mm.

*Mature leaf color.*—Upper side: green (RHS N137A). Under side: green (RHS 137A).

*Leaf base.*—Acute.

*Margin.*—Entire.

*Venation.*—Pattern: parallel. Color of midvein: upper side: green (RHS 139A). under side: green (RHS 139A).

Inflorescence description:

Appearance: Upright to slightly pendant, racemose inflorescence with bilaterally symmetrical flowers that open in succession beginning with the lowermost flower.

Raceme:

*Quantity per plant*.—About 2.

*Number of flowers per raceme*.—About 15.

*Length*.—About 28 cm.

*Diameter*.—About 50 cm.

Peduncle:

*Length*.—About 25 cm.

*Diameter*.—About 4 mm.

*Strength*.—Strong.

*Aspect*.—Upright.

*Texture*.—Glabrous and smooth.

*Color*.—Green (RHS 137A).

Buds:

*Height* (*from base to tip*).—About 20 mm.

*Diameter* (*at midpoint*).—About 18 mm.

*Shape*.—Asymmetric oval.

*Color*.—Red/purple (RHS 71A) with yellow/green (RHS 146C and RHS 146D).

*Orientation*.—Same as flowers (forward facing).

Flowering time: For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with flower buds and flowers. First flowers can be expected approximately 4 to 6 months after planting a plant with a leaf diameter of 3 to 5 cm. Flowers persistent.

Flowering longevity: On the plant: about 4 to 6 months; lastingness of cut flowers: has not been observed.

Fragrance: No fragrance.

Flower:

*Rate of opening*.—Flowers fully opened about 2 to 3 days after petal and sepal separation.

*Orientation at opening*.—Slanted upward and outward.

Figure 2:
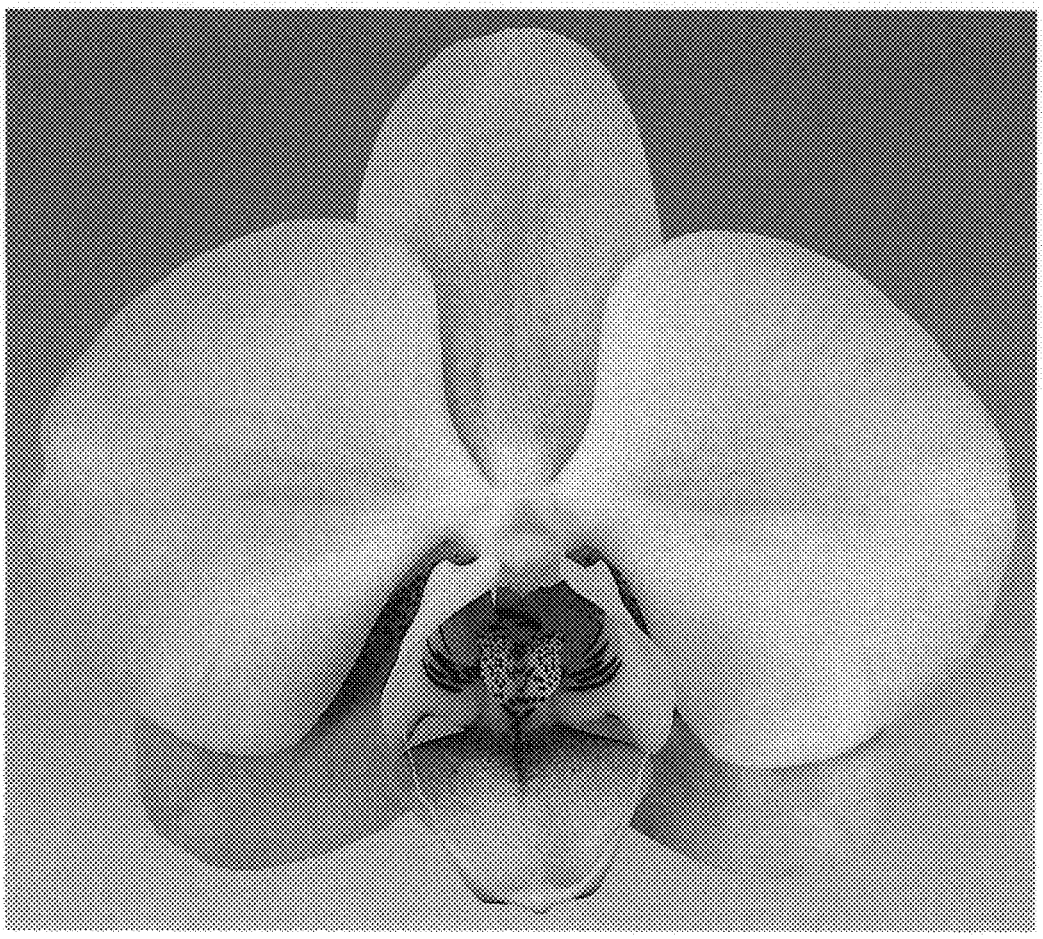
FIG. 2 shows a close-up view of the typical flower of 'Sweet Day'.
Figure 3:
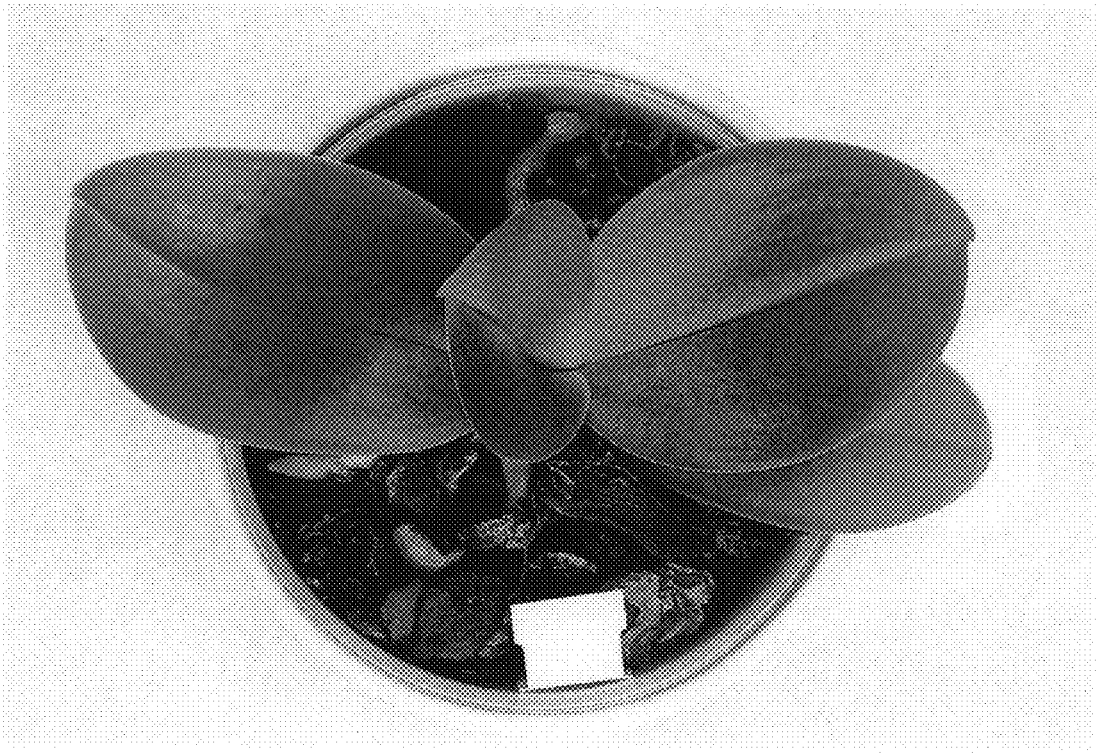
FIG. 3 shows a close-up view of the typical leaves of 'Sweet Day'.

*Shape*.—Typical shape of *Phalaenopsis*; see FIG. 2.

*Size* (*of single bloom*).—Height: about 70 mm. Diameter: about 80-90 mm.

*Quantity and arrangement*.—Three petals and three sepals. Arrangement of petals are free, not touching. Petals are more pronounced than sepals.

Petals:

*Arrangement*.—Inner whorl comprises 3 petals: 2 lateral petals and a labellum.

2 *lateral petals*.—Overall shape: broadly ovate and weakly cupped with a small cut at the top. Apex: round. Margin: entire and weakly undulate. Base: broadly ovate. Length: about 50 mm. Width: about 40 mm. Texture: Upper surface: smooth and satiny. Under surface: smooth and satiny. Color (when fully opened): upper side: centrally faint purple coloration/streaks (RHS 75A and RHS 75C) which gradually fades to white (RHS NN155D) towards the margin and base of petals. Under side: purple (RHS 75B and RHS 75C) with white (RHS NN155D). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin of the midlobe and lateral lobes: entire and weakly undulate. Apex of the midlobe and lateral lobes: rounded. Length midlobe: about 20 mm. Width midlobe (not flattened): about 20 mm. Length lateral lobe: about 18 mm. Width lateral lobe (not flattened): about 18 mm. Depth of tube created by lateral lobes of labellum: about 18 mm. Texture of the midlobe and lateral lobes: Upper & under surface: smooth and satiny. Color (when fully opened): Midlobe, upper side: the base is red/purple (RHS 59A and 71A) with a few red/purple spots (no stripes), which runs into white (RHS NN155D) with a purple haze (RHS 75B). In the corners some yellow (RHS 12A). Under side: main color is white (RHS NN155C). Edges are red/purple (RHS 71A) with a haze of yellow/green (RHS 145C). Lateral lobes, upper side: white (RHS NN155D) with at the base a few red/purple stripes (RHS 59A). The lower edges are yellow (RHS 12A) with red/purple (RHS 59A) and a red/purple haze (RHS70B). Under side: white (RHS NN155D) and the lower edges yellow (RHS 12A) with red/purple (RHS 59A) and a red/purple haze (RHS 70B). Cirrhi: about 20 mm. Color: white (RHS NN155D) with a purple haze (RHS 75B). Pestle (Callosities): Length: about 5 mm. Width (not flattened): about 5 mm. Color: yellow (RHS 12A) with red/purple stripes/spots (RHS 59A) in the middle some white (RHS 155B).

Sepals:

*Arrangement*.—Outer whorl comprises 3 sepals, one dorsal and two lateral sepals.

*Overall shape*.—Elliptical and weakly cupped.

*Margin*.—Entire and weakly undulate.

*Length*.—About 40 mm.

*Width*.—About 30 mm.

*Apex*.—Round.

*Texture*.—Upper and under surface: smooth and satiny.

*Color* (*when fully opened*).—Upper side, dorsal: purple (RHS 75A) with some purple (RHS 75C) with darker purple/violet veins (RHS N80B). The base, top and edges white (RHS NN155D). Lateral: purple (RHS 75C and RHS 75A) with at the base white (RHS NN155D) with a few red/purple stripes/spots (RHS 70A and RHS 70B). Under side, dorsal: purple (RHS 75A and RHS 75B) with a white haze (RHS NN155D). Lateral: purple (RHS 75A and RHS 75B) with a white haze (RHS NN155D).

Pedicel:

*Length*.—About 4 cm.

*Diameter*.—About 3 mm.

*Texture*.—Glabrous and smooth.

*Color*.—Yellow/green (RHS 146B) with purple (RHS 70A) and a haze of white (RHS NN155D).

Reproductive organs:

Arrangement: The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

Column:

*Length*.—About 7 mm.

*Diameter*.—About 4 mm.

*Color*.—The base is white (RHS NN155D) then purple (RHS 75A and RHS 75B).

Pollinia:

*Quantity*.—Two.

*Diameter*.—About 2 mm.

*Color*.—Yellow/orange (RHS 23A).

Ovary:

*Length*.—About 3 mm.

*Diameter*.—About 4 mm.

*Color*.—White (RHS NN155D).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Sweet Day', as illustrated and described herein.

* * * * *